(12) United States Patent
Yu et al.

(10) Patent No.: US 10,471,280 B2
(45) Date of Patent: Nov. 12, 2019

(54) RADIOSURGERY OF CANCERS IN THE BREAST AND THE HEAD USING A SINGLE MULTI-SOURCE GAMMA-RAY DEVICE

(71) Applicants: Xinsheng Yu, Pasadena, MD (US); Ying N. Niu, Rockville, MD (US); Peter Maton, Columbia, MD (US)

(72) Inventors: Xinsheng Yu, Pasadena, MD (US); Ying N. Niu, Rockville, MD (US); Peter Maton, Columbia, MD (US)

(73) Assignee: Xcision Medical Systems LLC, Columbia, MD (US)

( * ) Notice: Subject to any disclaimer, the term of this patent is extended or adjusted under 35 U.S.C. 154(b) by 197 days.

(21) Appl. No.: 15/651,593

(22) Filed: Jul. 17, 2017

(65) Prior Publication Data

US 2019/0015686 A1    Jan. 17, 2019

(51) Int. Cl.
*A61N 5/10*    (2006.01)

(52) U.S. Cl.
CPC .......... *A61N 5/1084* (2013.01); *A61N 5/1083* (2013.01); *A61N 5/1082* (2013.01); *A61N 2005/1095* (2013.01)

(58) Field of Classification Search
CPC ................ A61N 5/1083; A61N 5/1084; A61N 2007/0095; A61N 5/1082; A61N 2005/1097; A61N 2005/1095
See application file for complete search history.

(56) References Cited

U.S. PATENT DOCUMENTS

| | | | | |
|---|---|---|---|---|
| 2009/0080603 | A1* | 3/2009 | Shukla | A61B 6/025 378/25 |
| 2013/0142310 | A1* | 6/2013 | Fahimian | A61N 5/103 378/65 |
| 2014/0074076 | A1* | 3/2014 | Gertner | A61N 7/02 606/12 |
| 2016/0184605 | A1* | 6/2016 | Roberts | A61N 5/1014 600/7 |

OTHER PUBLICATIONS

Leksell L., Cerebral Radiosurgery. I. Gammathalanotomy in Two Cases of Intractable Pain, Acta Chir Scand. 1968; 134(8):585-595 (1968).
Yu et al, Gammapod—A New Device Dedicated for Stereotactic Radiotherapy of Breast Cancer, Med Phys. 40(5) (May 2013).

* cited by examiner

*Primary Examiner* — David P Porta
*Assistant Examiner* — Fani Boosalis
(74) *Attorney, Agent, or Firm* — Royal W. Craig; Gordon Feinblatt LLC

(57) ABSTRACT

A method of treating a cancerous region in a breast and/or in the head of a patient using a single radiosurgery device by placing the irradiation unit on an axle is disclosed. By pivoting the whole irradiation system, the treatment space can face different directions to accommodate the site of treatment. By continuously or sequentially pivoting the irradiation head unit and assigning different irradiation times to different pivoting angles, not only maximum degrees of expansion of the solid angle can be used for focusing the radiation beams to the target but also different regions of non-target tissues can have different shares of radiation doses based on how critical and radiation tolerant they are.

16 Claims, 5 Drawing Sheets

RADIOSURGERY OF CANCERS IN THE BREAST AND THE HEAD USING A SINGLE MULTI-SOURCE GAMMA-RAY DEVICE

BACKGROUND OF THE INVENTION

1. Field of the Invention

The present invention pertains to stereotactic radiosurgery of lesions in the breast and the head. Specifically, the present invention is a single multi-source gamma-ray irradiation system for radioablation of a target region in a human breast or a human head.

2. Description of the Background

Radiosurgery is surgery using radiation, that is, the destruction of precisely selected areas of tissue using ionizing radiation rather than excision with a blade. Radiosurgery enables ablation of a tumor with sub-milliliter precision. It has proven to be effective for all sites where a single, high dose can be safely delivered.

Radiosurgery has been defined and practiced as a single fraction therapy and its efficacy has been well-documented in the medical literature over the past three decades. The first 60Co Gamma-ray unit, now familiar as the Gamma Knife™, was introduced by Dr. Lars Leksell in 1968 as a radiosurgical tool for non-invasive neurosurgery. [Leksell L., Cerebral Radiosurgery. I. Gammathalanotomy In Two Cases Of Intractable Pain, Acta Chir Scand. 1968; 134(8):585-595 (1968); Leksell L: Cerebral Radiosurgery. I., Gammathalmotomy in Two Cases Of Intractable Pain, Acta Chir Scand 134:585-595 (1968)]. The modern versions of the design, now manufactured and marketed by Elekta Instrument AB of Sweden, contains 194-201 60Co sources, arranged on the surface of a hemispherical shell, each aimed at a single isocenter. The simplicity and high positional accuracy makes the Gamma Knife™ an ideal tool for its intended purpose. The use of a radiosurgical device for the treatment of tumors in the brain is illustrated in FIG. 1, where the hemispherical treatment space surrounds the patient's head and the patient is supported on a treatment couch in a supine position with head protruding into the treatment space to receive treatment. To date, most stereotactic radiosurgery has been performed on intracranial tumors using the Gamma Knifer™, and over the past three decades radiosurgery has become a routine procedure offered at medical facilities throughout the world.

The same principle has also been applied to stereotactic radiotherapy of breast cancer. [Yu et al, Gammapod-A New Device Dedicated for Stereotactic Radiotherapy of Breast Cancer, Med Phys. 40(5) (May 2013)]. Multiple (25-36) Co-60 sources are distributed over a range of latitudinal angles in a hemispherical structure to form multiple Gamma-ray beams aiming at the same isocenter. The entire structure is rotating during treatment, creating multiple non-overlapping conical arcs to achieve highly focused dose distribution.

FIG. 2 illustrates how the GammaPod™ is used for treating a tumor in a human breast. The treatment space of the GammaPod™ is facing upwards, and the patient is supported by a treatment couch in prone position with her breast pendent through an opening in the treatment couch, such that the breast can be placed in the treatment space with the tumor at the focal point of the radiation beams.

Both the Gamma Knife™ and GammaPod™ are devices specifically designed for treating one site (either the brain or the breast) and take advantage of the anatomical uniformity of that site for best treatment results. However, because the number of patients for a single site is limited, the device may not receive full utilization. For example, a large majority (>90%) of Gamma Knife™ systems in developed countries (US, EU, and Japan) are only used two days per week or less treating 5 patients per week or less due to lack of patients. This results in significant waste of resources. The same problem exists for GammaPod™. It is estimated that five hundred patients per year would be needed for full utilization of a GammaPod™. Combined, the foregoing facts result in significant underutilization and waste of resources.

What is needed is a multi-source gamma-ray radiosurgery system that is dual-use as this should greatly increase utilization and lower healthcare costs. It would also allow smaller hospitals to acquire such devices and offer this form of effective treatment, thereby improving accessibility.

However, administering an intense, short-duration course of treatment to a small volume in the breast or brain brings a unique set of challenges. Both the Gamma Knife™ and the GammaPod™ use multiple Cobalt-60 sources as the sources of the gamma-ray beams, and both rely on the principle of geometric focusing. By collimating the gamma-rays emitted by all the sources distributed in a solid angle toward a single point, maximum radiation dose is at the focal point and the surrounding regions get a fractional share of the radiation exposure burden. The greater the solid angle the rays are focused from, the greater the dose ratio between the target at the focal point and the surrounding normal structures. However, for practical reasons, the number of sources needs to be limited and they cannot be arranged over more than a few tens of degrees in latitudinal angles. This fact limits the dose ratio between the tumor and the surrounding normal structures, which reflects the key quality of radiosurgery treatments.

In view of the above, it is an object of the present invention to provide a single multi-source radiosurgery device to treat cancers in both the human breast and the human head. It is another object to enlarge the effective solid angle from which the gamma-ray beams are focused to maximize the dose ratio between the tumor and the surrounding normal structures.

SUMMARY OF THE INVENTION

Accordingly, it is an object of the present invention to provide a method of treating a cancerous region in a breast and/or in the head of a patient with a single multi-source gamma-ray radiosurgery device.

It is another object to provide a means to increase the solid angle from which the rays are focused.

It is still another object to provide a method of optimizing the weightings of each angle, or the time it spends at each angle to further improve the quality of the treatment based on the anatomic relationships between the target and its surrounding normal structures.

In accordance with the foregoing objects, the invention is a method and system for radioablation of a target region in a human breast and/or a human head, comprising an irradiating head unit for producing a radiation field, a flip mount for pivotally mounting said irradiating head unit for single-axis rotation and orientation of said radiation field within a range of at least 90 degrees, a patient support couch configured to support a patient in both a supine position for head treatment and a prone position for breast treatment, and an articulating support stand for moving said couch relative to said irradiation head unit along three axes and rotatable about these axes.

The flip mount comprises a pair of pin joints on opposing sides of the irradiating head unit, a linear drive, and a lever arm attached between one pin joint and the linear drive. The couch is supported on the articulating support stand which includes a carriage mounted on a track and a linear actuator for translation of the carriage along the track. In addition, a three-segment extension arm is mounted on the carriage, the arm having two pivot joints and a pair of actuators for articulating the three-segment extension arm at both pivot joints. A common control system in communication with all of the flip mount, irradiation head, articulating support and shutter to implement a treatment plan.

BRIEF DESCRIPTION OF THE DRAWINGS

Other objects, features, and advantages of the present invention will become more apparent from the following detailed description of the preferred embodiment and certain modifications thereof, in which.

DETAILED DESCRIPTION OF THE PREFERRED EMBODIMENT

Disclosed is a method and system for using a single multi-source stereotactic radiosurgery device to treat a cancerous region in either a human breast or a human head without compromising the quality of treatment as compared with its single site counterparts.

Figure 3:
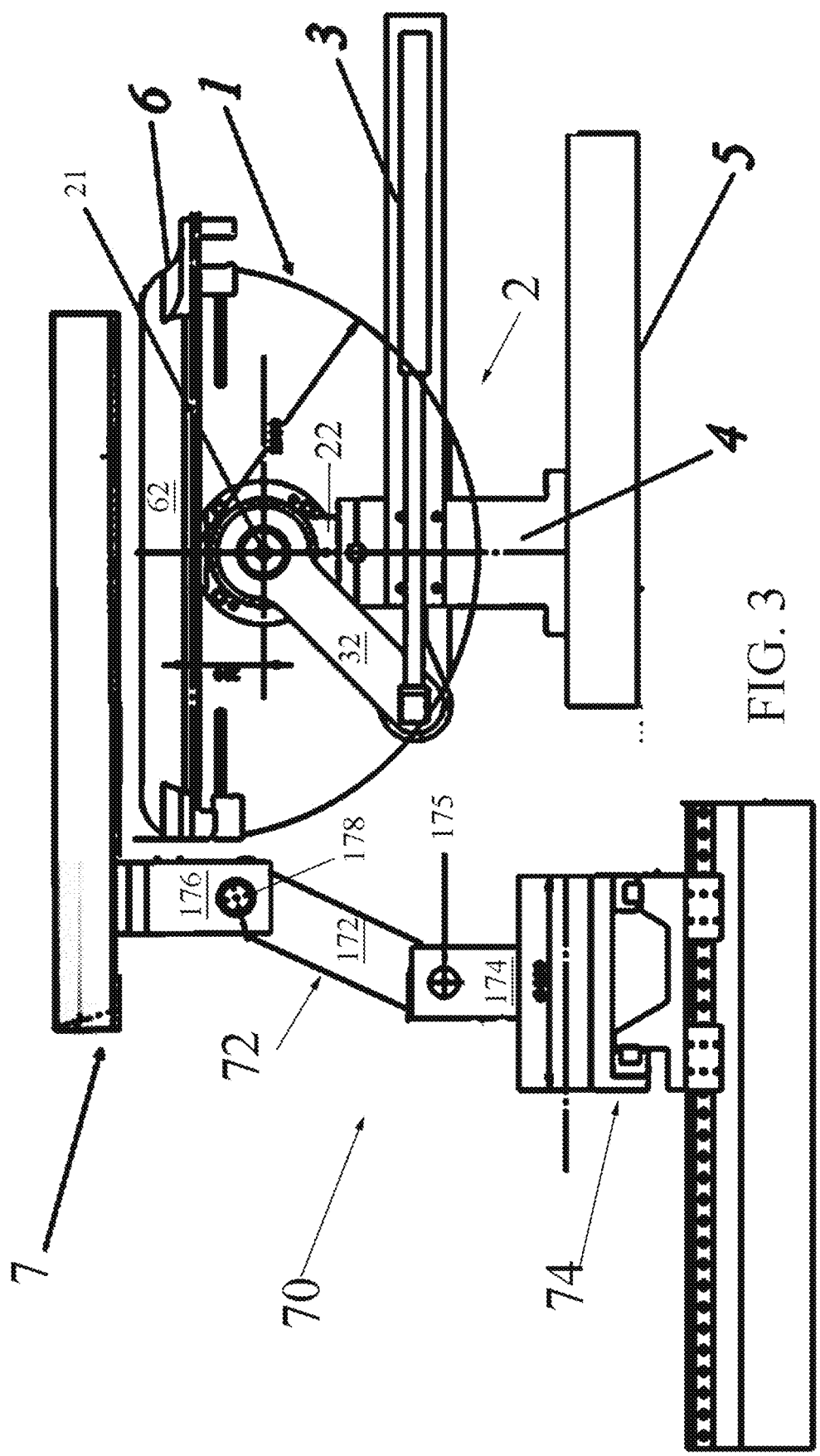
FIG. 3 is a side perspective view of a multi-source γ-irradiation unit according to an embodiment of the invention.
Figure 4:
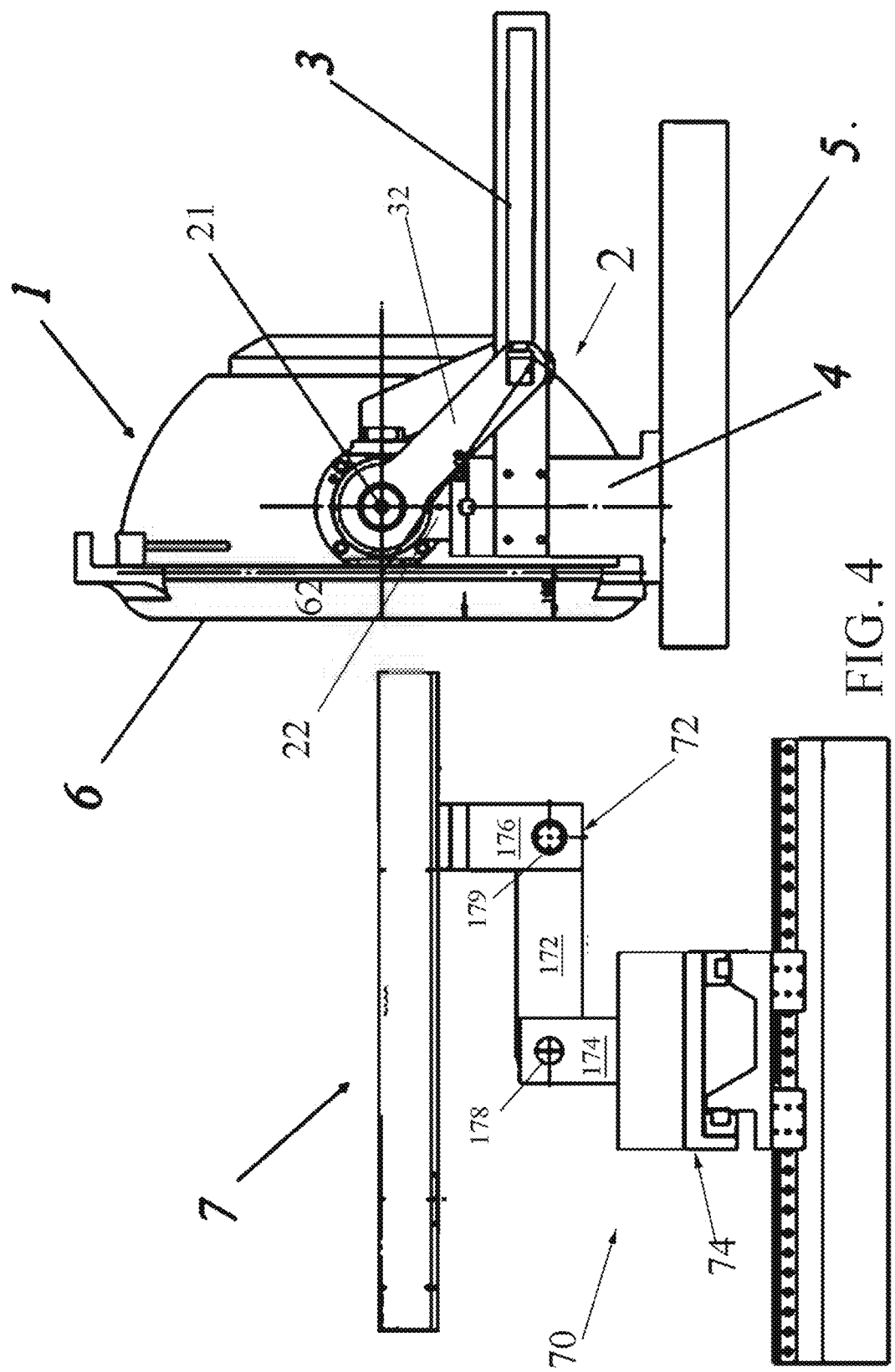
FIG. 4 is a side perspective view of the same multi-source γ-irradiation unit of FIG. 3 used for treating the brain by supporting the entire irradiation unit on two rotatable, coaxial joints and make it pivotable.

FIGS. 3 and 4 are side perspective views of the multi-source γ-irradiation unit of the invention, FIG. 3 illustrating configuration for treating the breast and FIG. 4 for the brain.

The system includes a patient support couch 7, operable to support a patient in a supine position during radiosurgery. The couch 7 is mounted on an articulating support stand 70 that moves the couch 7 into and out of a field of radiation along five-degrees of motion, to support a patient in prone position with sufficient height and forward reach for breast treatment and also a patient in supine position with proper height and extension for treating a tumor in the head.

Importantly, the couch 7 must have a known geometric relationship with respect to the irradiation head unit 1 in each case. Therefore, support stand 70 is preferably dual-controlled: 1) manually by a couch operator using a control keypad; and/or 2) automatically by a programmable controller that also robotically control operation of irradiation head unit 1.

In an embodiment the couch support stand 70 is configured with a linear drive assembly 74 for linear translation along a horizontal axis (i.e., x axis). Additionally, the couch 7 is configured with an extension arm 72 capable of translation along both vertical and horizontal axes (i.e., x and y axes) as well as rotation along the third z axis. The extension arm 72 further comprises three segments pivotally connected end-to-end at two actuated pivot joints 175, 178. As in conventional couch designs, a hydraulic or other suitable lifting system is utilized to move the extension arm 72. If hydraulic, hydraulic joint cylinders or other suitable actuators may be used as known in the art. One segment 176 is connected to and supports the couch 7, one 174 is connected to the linear drive assembly 74, and an intermediate segment 172 joins segments 174, 176.

Figure 1:
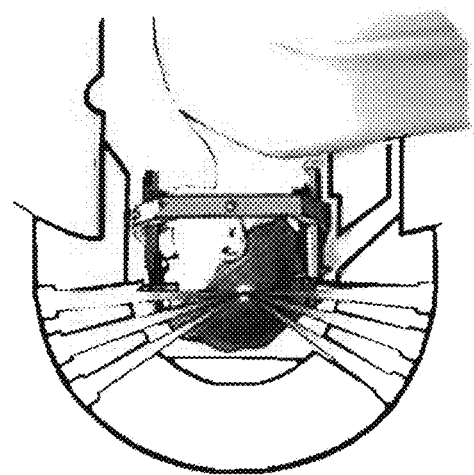
FIG. 1 is a side perspective view of a prior art multisource γ-irradiation unit with the entrance to the treatment space facing sideways for treating a tumor inside a human head when the patient is supported on a treatment couch in supine position.
Figure 2:
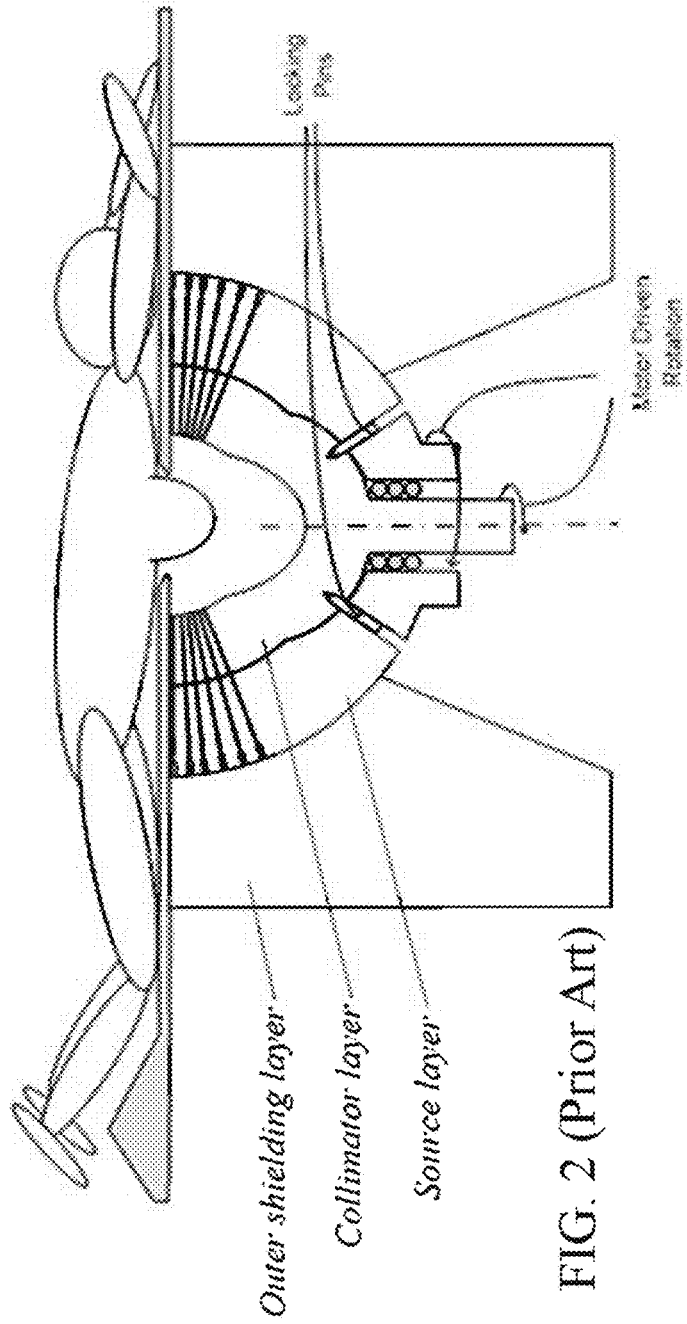
FIG. 2 is a side perspective view of a prior art multi-source γ-irradiation unit with the entrance to the treatment space facing upwards for treating a tumor inside a human breast when the patient is in prone position.

The system also includes an articulating irradiation head unit 1 for radiosurgery of the patient while supine atop the patient support couch 7. The irradiation head unit 1 may be a conventional Gamma Knife™ or GammaPod™ head unit in which multiple Cobalt-60 sources emit a hemispheric array of pencil-shaped gamma-ray beams of approximately 30 curies (1.1 TBq), all within a heavily shielded assembly as seen in FIG. 1. The irradiation head unit 1 relies on geometric focusing by collimating the gamma-rays in a solid angle toward a single focal point, or "target point" in the patient's brain. The patient wears a specialized helmet that is surgically fixed to the skull, so that the brain tumor remains stationary at the target point of the gamma rays. An ablative dose of radiation is thereby sent through the tumor in one treatment session, while surrounding brain tissues are relatively spared. The irradiation head unit 1 will typically include an outer shielding layer, a layer containing the distributed radiation sources, and an inner collimator layer as shown in FIG. 2.

Rather than fixing the orientation of the irradiation head unit 1 and hence the treatment space, as in the prior art, the entire irradiation head unit 1 is pivotally supported on a 90° flip mount 2 that rotates the irradiation head unit 1 about the third z axis relative to the couch 7. In an embodiment, the flip mount 2 comprises two coaxial pin joints 21, one on each side, configured such that the entire irradiation unit 1 is pivotable about the z axis. The two coaxial pin joints 21 establish a one-degree-of-freedom kinematic pair providing single-axis rotation of irradiation head unit 1. Each pin joint 21 comprises a pin extended from irradiation head unit 1 and rotatably journaled into a stationary yoke 22 via bushings. Preferably, the two coaxial pin joints 21 are located at the center of gravity of irradiation head unit 1.

In an embodiment the couch support stand 70 is configured with a linear drive assembly 74 for linear translation along a horizontal axis (i.e., x axis). The linear drive assembly 74 may be a track and rail system actuated by a linear actuator, or a linear gear system or the like.

For the convenience of description, the pivoting angle shall be denoted to be 0 degrees when the rotating axis of the irradiation head unit 1 is vertical, as in FIG. 3, and 90 degrees when the rotation axis is horizontal as in FIG. 4. Importantly, there is no physical axle traversing the irradiation head unit 1, so that the functions of the irradiation head unit 1 are not affected. The two yokes 22 supporting the two pin joints 22 are in turn supported by two columns 4 (one on each side), which columns 4 rest on a common base frame 5.

In accordance with the invention the irradiation head unit 1 is equipped with aperture shielding door 6 configured to cover the treatment space when the system is not being used for treating a patient. Door 6 preferably comprises a support ring 62 attached around the aperture of the radiation head unit 1 and supporting a solid door 64 closable across the support ring 62 to shield leakage radiation coming out of the treatment space when the system is not treating a patient. One skilled in the art will understand that the door 64 may take any of a variety of other configurations including slidable, pivotable (single or bifold) or the like. The door 6 is open in the direction parallel to the viewing direction of FIGS. 3-4. As seen in FIG. 3 the entrance to the treatment space faces upwards for treating a tumor inside a human breast when the patient is in prone position. As seen in FIG. 4, when the irradiation head unit 1 is facing sideways the head of a patient lying on a treatment couch in the supine position enters the treatment space and thereby a tumor inside a human head can be treated.

One skilled in the art will understand that there are many ways to pivot the irradiation head unit 1. In the preferred embodiment a linear actuator 3 is mounted to one of the columns 4 horizontal to base frame 5, and the linear actuator 3 is connected to the end of a lever arm 32. The lever arm 32 runs to a yoke which is affixed onto the end of one of the pins of the two coaxial pin joints 21, and thereby translates linear motion of actuator 3 into rotation of radiation head unit 1. However, those having ordinary skill in the art may select other suitable pivot methods, such as using a gear or a ball-screw, or otherwise.

The couch 7 should also be able to adapt to the treatment of both a human breast and a head. For the former, couch 7 is configured flat to allow the patient to rest prone, with one opening to allow the affected breasts to extend through the table such that the breast can enter the treatment space of the head unit 1 oriented upward below the couch 7. For the latter, couch 7 is configured flat to allow the patient to rest supine such that the head can enter the treatment space of the head unit 1 oriented sideward toward the couch 7. This requires a mechanically-adjustable, electrically or pneumatically driven table with height-adjustability and interchangeable backrest. One skilled in the art will understand that the patient supporting and moving couch 7 can have alternative designs or be a fully robotic couch with multiple axes of rotation and translation.

Both the flip mount 2 that rotates the irradiation head unit 1 and the couch support stand 70, as well as the treatment as a whole, are coordinated and controlled by a treatment control system 8, a computer system that controls the motion and irradiation for both the irradiation unit 1 and the robotic couch 7.

Figure 5:
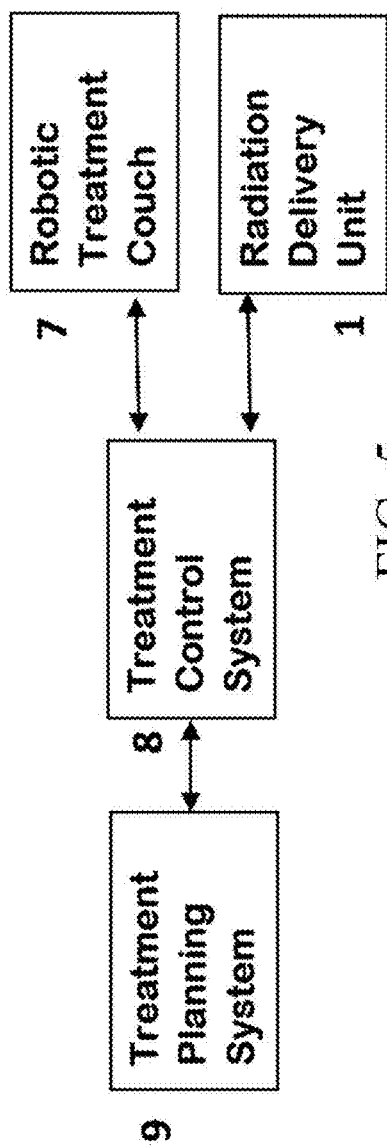
FIG. 5 is a block diagram of the control system architecture for the multi-source γ-irradiation unit according to the invention.

FIG. 5 is a block diagram of the architecture for the multi-source γ-irradiation unit according to the invention, including treatment control system 8. Treatment control system 8 may be any suitable computer having non-transitory computer memory connected to the treatment planning system 9, and running application software comprising computer instructions stored on the non-transitory computer memory for executing the treatment plan. Typically, a treatment plan will be designed using the treatment planning system 9, another computer. The plan from treatment planning system 9 is uploaded to the treatment control system 8 electronically, such as through a serial connection or a private network link. The treatment plan is structured as a collection of control points, each specifying the coordinates of all axis, collimator size or index, the pivot angle, the beam status, and the time duration. The treatment control system 8 converts the treatment plan to control signals for all the axis and beam on/off controls of the irradiation head unit 1, as well as the flip mount 2, couch support stand 70 and the irradiation head unit 1. The geometric relationship of the robotic couch 7 and the irradiation head unit 1 is calibrated at the time of commissioning and entered into and modeled by the treatment control system 8.

Geometric focusing is the main principle of radiosurgery. When hundreds or thousands of beams are focused to a single focal point, the point is being irradiated by all the beams, while the surrounding regions are being irradiated only by some of the beams. For practical reasons, the number of sources and the solid angle within which the sources are distributed are both limited. The sources cannot be placed too close to 0 degrees latitude because there must be sufficient distance from the shallowest sources to the surface of the treatment space in order to provide sufficient radiation shielding. Placing a source too close to the surface of the irradiation unit means reducing the space needed for placing shielding materials. Moreover, the beams often need to be angled towards surface of the treatment space so that the patient need not go deep into the treatment space, which often has very limited depth due to physical constraints. It is also not desirable to place the sources at very large latitudes for irradiating either the breast or the head. In breast treatments, beams aiming at the focal point from large latitudes also aim at the chest wall, the lung and the heart. In head treatments, beams at large latitudes are aiming substantially in the cranial-caudal direction, causing all the energy carried by the photons to be deposited in the patient. These practical limitations place practical limits on the degree of geometric focusing. Because of these limitations and considerations, the latitudinal range of sources distributions in commercially available multi-source radiosurgery systems is from 20 degrees to 40 degrees. The limitation of the latitudinal range of source distribution places a limit on the quality of treatments by such multi-source radiosurgery devices. For a given target of a fixed size and shape in a rounded structure such as the breast and the head, the ratio of energy carried by the gamma-ray photons deposited in the target and in the surrounding normal tissues is approximately a constant regardless of the number of beams used. Therefore, the greater the solid angle from which the beams are focused from, the greater volume of non-target tissues are involved in sharing the radiation burden. As the result, the radiation doses, expressed as energy deposited per mass of medium, to the non-target tissues are reduced. The present system places the multi-source focusing collimator of irradiation head unit 1 on a virtual axle, such that the direction of entry to the treatment space can be oriented at any angle. This provides a means to increase the solid angle from which the rays are focused and alleviates the physical limitations on source distribution. The number of radiation sources can be reduced without lowering the treatment quality, resulting in substantial cost savings. This also facilitates optimization of the weightings of each angle, or the time spent at each angle to further improve the quality of the treatment based on the anatomic relationships between the target and its surrounding normal structures.

Figure 6:
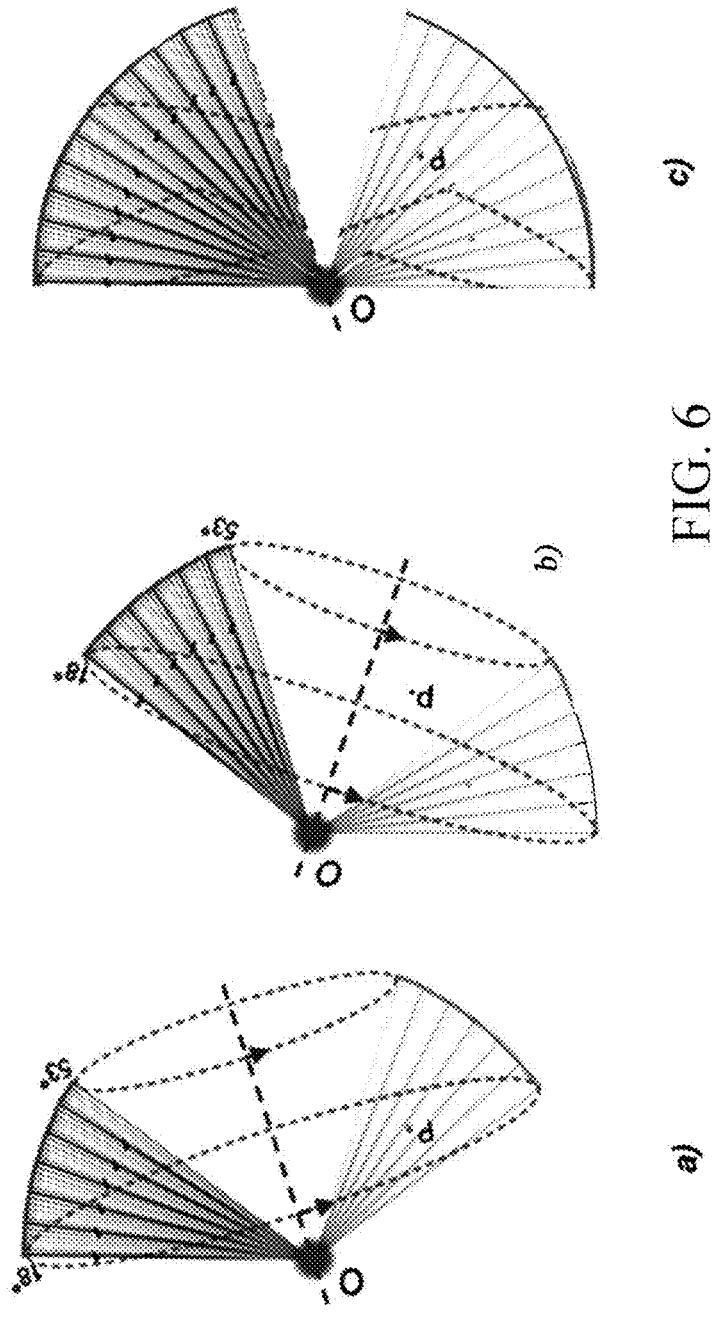
FIG. 6 is a perspective sequential illustration of the principle of geometric focusing and how rotating the unit can increase the solid angle, from which the gamma-rays are focused to the target.

FIG. 6 is a perspective sequential illustration of the principle of geometric focusing that illustrates how rotating the irradiation head unit 1 can increase the solid angle, from which the gamma-rays are focused to the target. By allowing the entire irradiation head unit 1 to pivot, multiple pivoting angles can be used in a single treatment session to effectively increase the latitudinal angles and thus the degree of geometric focusing without increasing the number of sources.

FIG. 6 (a and b) illustrate a multisource gamma-ray radiosurgery system with sources distributed from 18 degrees to 53 degrees at a pivoting angle of +108 degrees and +72 degrees, respectively. In the example illustrated by FIG. 6(a), the sources are distributed 360 degrees in longitude, i.e., all around, and from 18 degrees to 53 degrees in latitude, representing a realistic practical limit for such multisource radiosurgery devices. The focal point "O" is irradiated by all the beams at all the time, while a non-target tissue at point "P" is irradiated by only a few beams. If the device is not pivotable, point "P" will receive a fraction "f" of the dose received at "O". However, consider that irradiation head unit 1 is pivotable as described above and there is no collision with the patient under both conditions depicted in FIGS. 6(a) and 6(b). If point "O" is irradiated to the same dose but with half the time given at the condition of FIG. 6(a) and the other half of the total treatment time given at the condition of FIG. 6(b), then the equivalent focusing geometry would be that of FIG. 6(c), as if the sources were distributed between 0 degree latitude to 72 degree latitude. The effects on non-target tissue can be seen by the dose received at point "P", which is not in the direct beams during the treatment under conditions of FIG. 6(b) and therefore gets 0.5f of the dose at "O", i.e., only half of the dose as compared to only using the configuration of FIG. 6(a). The example illustrated by FIG. 6 is facilitated by sequentially pivoting the irradiation head unit 1 to +108 and +72 degrees and assigning each angle 50% of the total treatment time to double the solid angle of focus (FIG. 6(c)).

More generally, not all the tissues and organs surrounding the target are the same and should be treated equally. Different tissues may have different radiosensitivity and radiation tolerance. Some may be more functionally critical than others. Therefore, it is generally desirable in radiation treatments that we take such anatomical tolerance and criticality into consideration. By continuously or sequentially pivoting the irradiation head unit 1 and assigning different irradiation times to different pivoting angles, not only maximum degrees of expansion of the solid angle can be achieved but also different regions of non-target tissues can have different shares of radiation doses based on how critical and radiation tolerant they are. The range of pivoting is limited by the physical arrangement of the patient supported on the couch and the irradiation head unit 1 such that the device needs to have a clearance from the patient's body and the couch to avoid colliding with the patient or the supporting couch.

The considerations of sparing different non-target tissues differently while still satisfying the dose coverage of the target can be very complex and there can be conflicting requirements. Such tasks are best performed by a computer rather than manually by a human planner. In general, a computerized treatment planning system 9 is used to plan the treatment delivery. The computerized treatment planning system 9 can either allow the operator to manually set the angles and to edit the weights of each pivot angle or, more preferably, automatically optimize the pivot angles and their weights. Planning methods currently used for the treatment of intracranial lesions (Shepard et al., Intl J. of Radiat. Oncol. Biol. Physics 56(5): 1488-1494 (2003); and Yu et al., Tech. in Cancer Res. and Treatment 2(2): 93-104 (2003)) cannot optimize such pivot angles because pivoting the entire irradiation unit has never been proposed before. Adding the pivot angle to the optimization process introduces additional parameters to be optimized and makes the plan optimization more computationally intensive.

Figure 7:
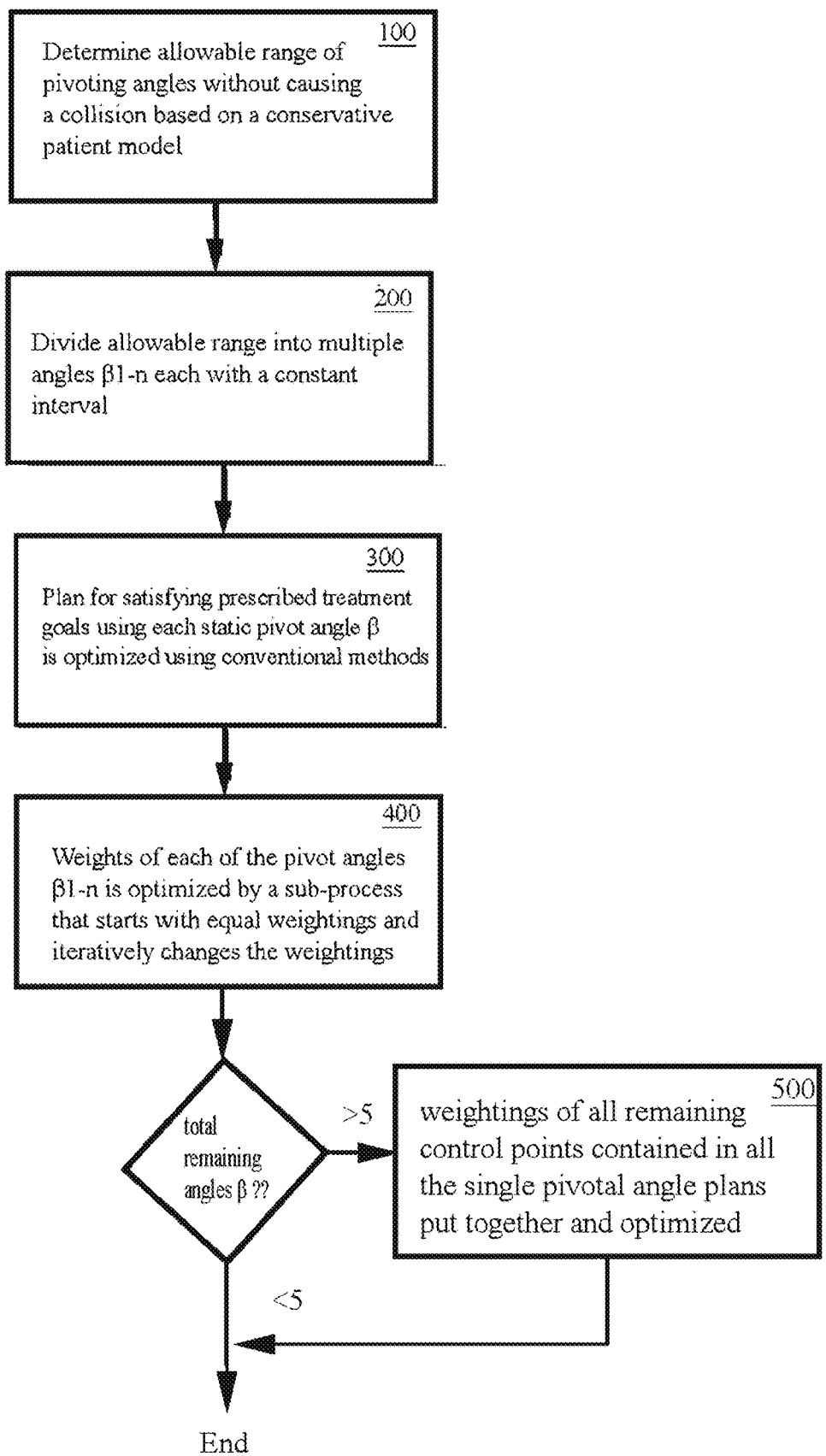
FIG. 7 is a flow chart illustrating the steps of the optimizing the pivot angle.

FIG. 7 is a flow chart illustrating the steps of the optimizing the pivot angle by a computer. Since optimizing a radiation treatment plan are well understood and already being used in current clinical practice, the focus of the discussion and the novel aspect is in how to optimize the pivot angles of the irradiation head unit 1. As with other treatment planning optimization, the target and critical structures would have been delineated by the physician and the prescribed dose to the target and the limiting dose to the critical structures have been specified. Initially, a cost function is constructed to reflect the goodness (quality) of the treatment plan. This may be accomplished by inverse treatment planning as known in the art, with a dose-based model to achieve accurate dose distribution.

In the first step 100, the allowable range R of pivoting angles without causing a collision is conservatively determined from a conservative patient model. For example, for a head treatment model, we would model the patient with the biggest head size, shortest neck, and largest chest size. Alternatively, such range R can also be determined from the three-dimensional images sets of the patient and the digital model of the device.

In step 200, the allowable range R is be divided into multiple angles, $\beta_1, \beta_2, \ldots \beta_n$, each with a constant interval.

In step 300, the plan for satisfying the prescribed treatment goals using each static pivot angle $\beta_1, \beta_2, \ldots \beta_n$ will be optimized using conventional methods and optimization algorithms. The resulting dose distributions for each of the plans corresponding to each of the pivot angles $\beta_1, \beta_2, \ldots \beta_n$ are stored, as well as the dose distribution for each of the control points contained in each single pivot angle plan.

In step 400, the weights of each of the pivot angles $\beta_1, \beta_2, \ldots \beta_n$ are optimized by an conventional optimization algorithm to find the weight at each of the pivot angles $\beta_1, \beta_2, \ldots \beta_n$ that best matches all the input criteria sub-process that starts with equal weightings and iteratively changes the weightings to optimize. The dose is the weighted sum of the dose distributions optimized for each of the pivot angles $\beta_1, \beta_2, \ldots \beta_n$. During the process, any pivot angle $\beta_i$ with weights falling below a predetermined threshold is eliminated.

The optimization process stops when no further improvement to the plan quality as governed by the cost function can be made. If the total remaining angles are small, say five or less, the optimization process ends. The treatment will be delivered with these pivot angles successively.

If the total number of remaining angles are large, it would not be practical to make the treatment time for each pivot angle so short for reliable delivery. In such cases, step 500 is needed. In step 500 the weightings of all remaining control points contained in all the single pivotal angle plans will be put together and optimized. The purpose is to eliminate the total number of control points for reliable delivery. The same algorithm as for the angle weight optimization in Step 400 can be used for optimizing the weightings of control points at step 500. Control points with weights fall below a threshold will be eliminated successively until the total number of control points drops to a manageable range of about 500.

It is important to note that the pivoting axis may not necessarily coaxial with the focal spot. In general, and it is even desirable, that the focal spot and the two pivoting joints are not coaxial. However, as long as the distance of the focal point to the pivoting axis is known, the spatial location of the focal spot is known for all pivoting angles and the control system will direct the robotic couch to align the point of treatment with the focal point.

It should now be apparent that the present invention further provides a dedicated treatment planning system, which, in addition to optimizing the focal spot sizes and locations to be used based on the three-dimensional (3-D) CT and/or MRI images, also optimizes the pivot angles and their weights. The system, which models the radiation precisely, comprises a computer, supporting circuitry, and various software modules including, but not limited to, DICOM import of images, stereotactic localization involving the use of fiducial localization frames, target delineation involving the use of contouring tools to delineate the gross tumor and/or the intended treatment volume, dose calculation, determining the range of allowable pivot angles to avoid collision with patients, optimization algorithms for optimizing the location of the focal spots for each possible pivot angle and the time duration of each focal spot and dose-volume analysis, dose display of the final dose in Gy, and printing of 2-D and 3-D dose displays and a plan summary. The dose displays can be printed along with a treatment plan summary, which can include, for example, the treatment time at each focal spot at a particular pivot angle, the coordinates of the couch for each focal spot at a given pivot angle.

The foregoing examples serve to illustrate the present disclosure. The examples are not intended to limit the scope of the claimed invention in any way. The terms and expressions, which have been employed, are used as terms of description and not of limitation. In this regard, where certain terms are defined and otherwise described or discussed elsewhere herein, all such definitions, descriptions, and discussions are intended to be attributed to such terms. There also is no intention in the use of such terms and expressions of excluding any equivalents of the features shown and described or portions thereof.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth herein.

We claim:

1. A single multi-source gamma-ray irradiation system for radioablation of a target region in a human breast and in a human head, comprising:
   a irradiating head unit for producing a radiation field;
   a flip mount for pivotally mounting said irradiating head unit for single-axis rotation and orientation of said radiation field within a range of at least 90 degrees;
   a patient support couch configured to support a patient in a supine position; and
   an articulating support stand for multi-axis movement of said couch relative to said irradiation head unit.

2. The single multi-source gamma-ray irradiation system according to claim 1, further comprising a radio-opaque shutter attached to said irradiating head unit for selectively blocking said radiation field.

3. The single multi-source gamma-ray irradiation system according to claim 2, wherein said shutter comprises closable doors.

4. The single multi-source gamma-ray irradiation system to claim 3, wherein said flip mount comprises a lever arm attached between one of said pin joints and said linear drive assembly.

5. The single multi-source gamma-ray irradiation system according to claim 1, wherein said flip mount comprises a pair of pin joints on opposing sides of said irradiating head unit.

6. The single multi-source gamma-ray irradiation system according to claim 1, wherein said articulating support stand comprises a linear drive assembly configured for linear translation of said patient support couch along at least one axis, and a pivot-drive assembly for moving said patient support couch relative to said irradiation head unit.

7. The single multi-source gamma-ray irradiation system to claim 1, further comprising a control system in communication with both said flip mount, irradiation head and articulating support and programmed with software for execution of a treatment plan by common control and synchronized motion thereof.

8. The single multi-source gamma-ray irradiation system to claim 7, wherein said control system is also in communication with said shutter.

9. A method of operating the pivotally mounted multi-source gamma-ray radiosurgery system of claim 1, comprising pivoting the said radiation head unit about the said pin joint within an angular range during irradiation of a patient.

10. The method according to claim 9, wherein said pivoting said radiation head unit during irradiation comprises continuous pivoting with constant or varying speed at different pivoting angles.

11. The method according to claim 9, wherein said pivoting of said radiation head unit during irradiation comprises sequential intermittent pivoting with constant or varying dwell times at different pivoting angles.

12. The single multi-source gamma-ray irradiation system according to claim 1, wherein said range includes an orientation wherein a focal axis of said head unit is substantially parallel to a lengthwise axis of said couch.

13. A method of optimizing a treatment plan for using a multisource gamma-ray radiosurgery system to irradiate a target in a patient's head or in a patient's breast, comprising optimizing the treatment plan as a function of a plurality of parameters including at least multiple pivot angles of a radiation head unit, dwell times at each of the pivot angles, focal spot sizes and focal spot locations.

14. The method of claim 13 in which the pivot angles of a radiation head unit of and the dwell times at each of the optimized pivot angles are determined through the steps of:
   determining the range R of feasible angles for pivoting said radiation head unit about an axis perpendicular to its focal axis, within which it is not possible for the said radiation head unit to collide with the patient or the patient support couch and structure;
   dividing said calculated allowable range R into multiple equal smaller pivot angles $\beta_1, \beta_2, \ldots \beta_n$ and initially assigning equal weightings at each of the pivot angles;
   iteratively changing the weightings at each of the pivot angles and accepting the change if plan quality improves and rejecting such change if plan quality worsens until no further improvement of plan quality is possible;
   iteratively eliminating pivoting angles with weightings lower than a predetermined threshold until no further improvement of plan quality is possible; and
   selecting between continuous pivoting delivery and sequential pivoting delivery based on the number of remaining pivoting angles and separation there between; and
   constructing a deliverable treatment plan.

15. The method of claim 14, wherein said step of calculating an allowable range R of pivoting angles for pivoting said radiation head unit is based on digital models of the patient and the said multisource gamma-ray radiosurgery system.

16. The method of claim 14, wherein said step of calculating an allowable range R of pivoting angles for pivoting said radiation head unit is based on three-dimensional image sets of the patient and the digital representations of the said multisource gamma-ray radiosurgery system.

* * * * *